United States Patent [19]

Vicenzi et al.

[11] Patent Number: 4,905,688
[45] Date of Patent: Mar. 6, 1990

[54] PORTABLE LIGHT WEIGHT COMPLETELY SELF-CONTAINED EMERGENCY SINGLE PATIENT VENTILATOR/RESUSCITATOR

[75] Inventors: Reno L. Vicenzi, Moreno Valley; Thomas R. Findlay, III, Monrovia, both of Calif.

[73] Assignee: Figgie International Inc., Richmond, Va.

[21] Appl. No.: 312,023

[22] Filed: Feb. 16, 1989

[51] Int. Cl.⁴ ............................................. A61M 16/00
[52] U.S. Cl. ........................... 128/204.21; 128/204.25; 128/205.12; 128/201.25
[58] Field of Search ................... 128/201.28, 204.21, 128/204.18, 204.25, 205.11, 205.12, 205.14, 205.15, 205.16, 205.18, 205.24, 205.27, 206.12, 206.15, 201.25

[56] References Cited

U.S. PATENT DOCUMENTS

| | | | |
|---|---|---|---|
| 3,976,064 | 8/1976 | Wood et al. | 128/204.21 |
| 4,206,754 | 6/1980 | Cox et al. | 128/204.21 |
| 4,243,029 | 1/1981 | Apple | 128/204.21 |
| 4,506,667 | 3/1985 | Ansite | |
| 4,587,967 | 5/1986 | Chu et al. | 128/204.21 |
| 4,592,349 | 6/1986 | Bird | 128/204.25 |
| 4,622,963 | 11/1986 | Ansite | |
| 4,637,386 | 1/1987 | Baum | 128/204.21 |
| 4,651,731 | 3/1987 | Vicenzi et al. | |
| 4,682,591 | 7/1987 | Jones | 128/204.25 |
| 4,788,974 | 12/1988 | Phuc | 128/204.21 |
| 4,805,613 | 2/1989 | Bird | 128/204.25 |
| 4,827,922 | 5/1989 | Champain et al. | 128/204.21 |
| 4,838,257 | 6/1989 | Hatch | 128/204.18 |

Primary Examiner—Eugene H. Eickholt
Attorney, Agent, or Firm—Edwin T. Bean, Jr.; Martin G. Linihan; John C. Thompson

[57] ABSTRACT

A portable light weight completely self-contained emergency single patient ventilator/resuscitating apparatus (10) usable at the scene of an emergency by persons with minimal training. The apparatus (10) includes a housing assembly (12) which supports a solid state oxygen generator which also acts as a power supply, the generator being in the form of a chlorate candle (20). The housing additionally supports a pump (90) in the form of a venturi ejector, a two-position valve (92), and suitable primary controls (93) which are utilized to control the inspiratory:expiratory (I:E) ratio, the inspiratory time, the expiratory time, the breaths per minute, the flow rate, the tidal volume, the minute volume, etc. Various fluid passageways (54, 58, 116, 118) interconnect the candle with the valve, and additional fluid lines (120, 138, 140, 146, 148) interconnect the valve with the pump and primary controls. The primary controls include a fixed volume timing chamber (132) which is disposed about the venturi ejector. The housing is provided with a void (98) adjacent the timing chamber, which void acts as an accumulator during the expiratory cycle. While the two-position valve is normally automatically switched between inspiratory and expiratory positions by the pirmary control, it may be manually switched from its expiratory position to its inspiratory position against full pilot line pressure by a secondary control including a push button (152) or the like when the operator desire to give extra breaths or sigh breaths. In addition, the push button can be so positioned that the valve may be maintained in its inspiratory position, which may be desirable when the patient is breathing on his own and only requires extra oxygen over that which he would normally receive from ambient air.

23 Claims, 5 Drawing Sheets

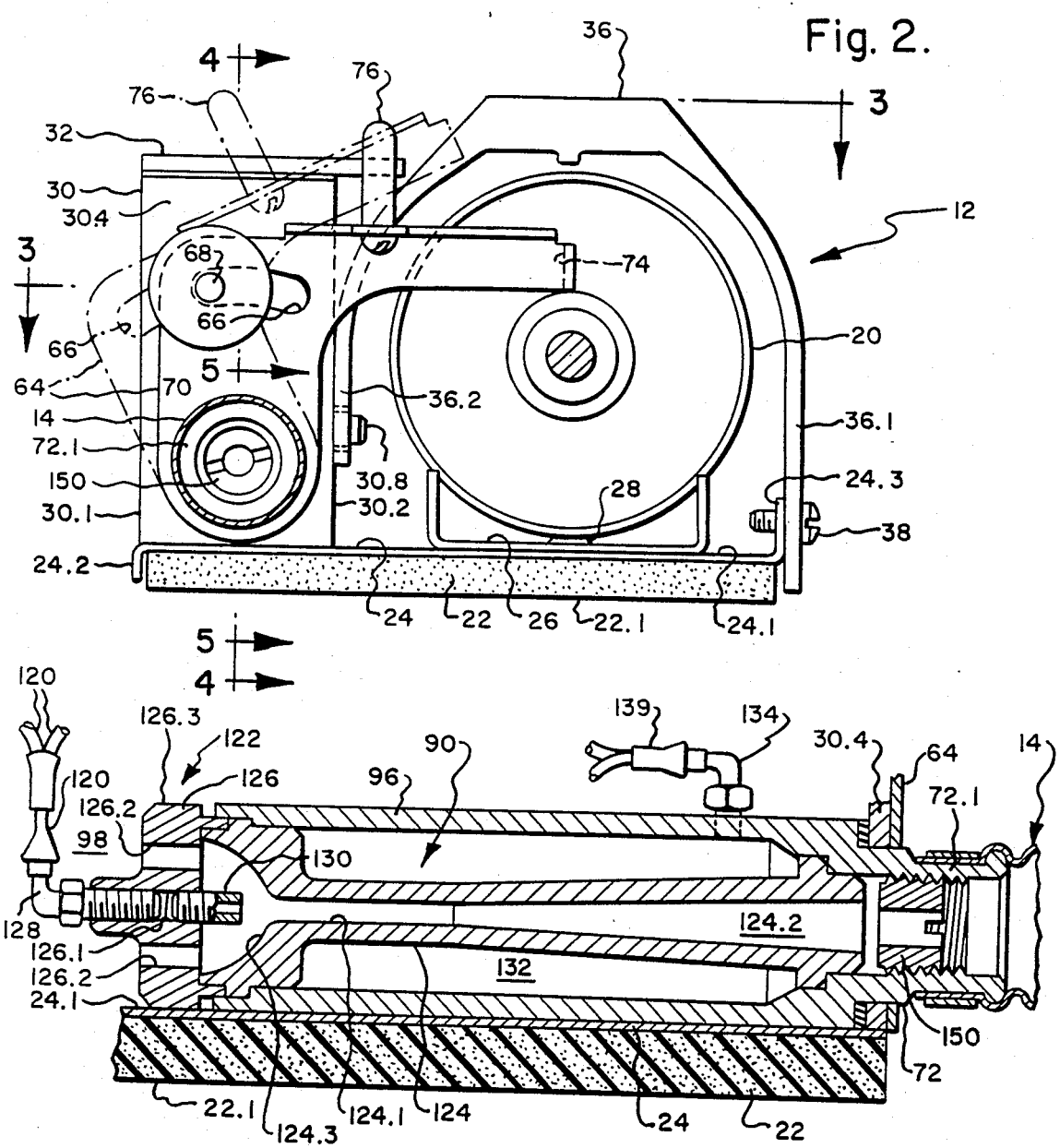

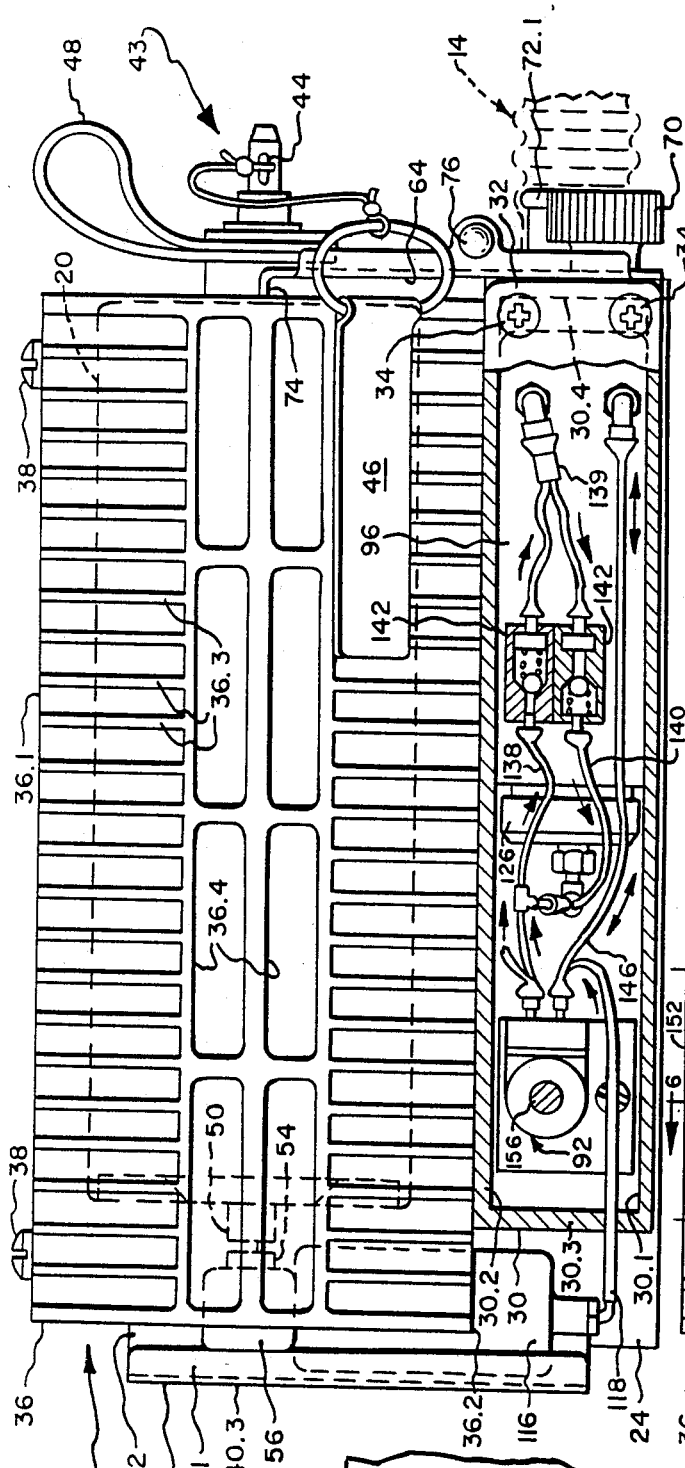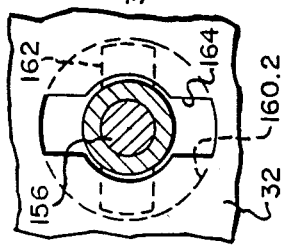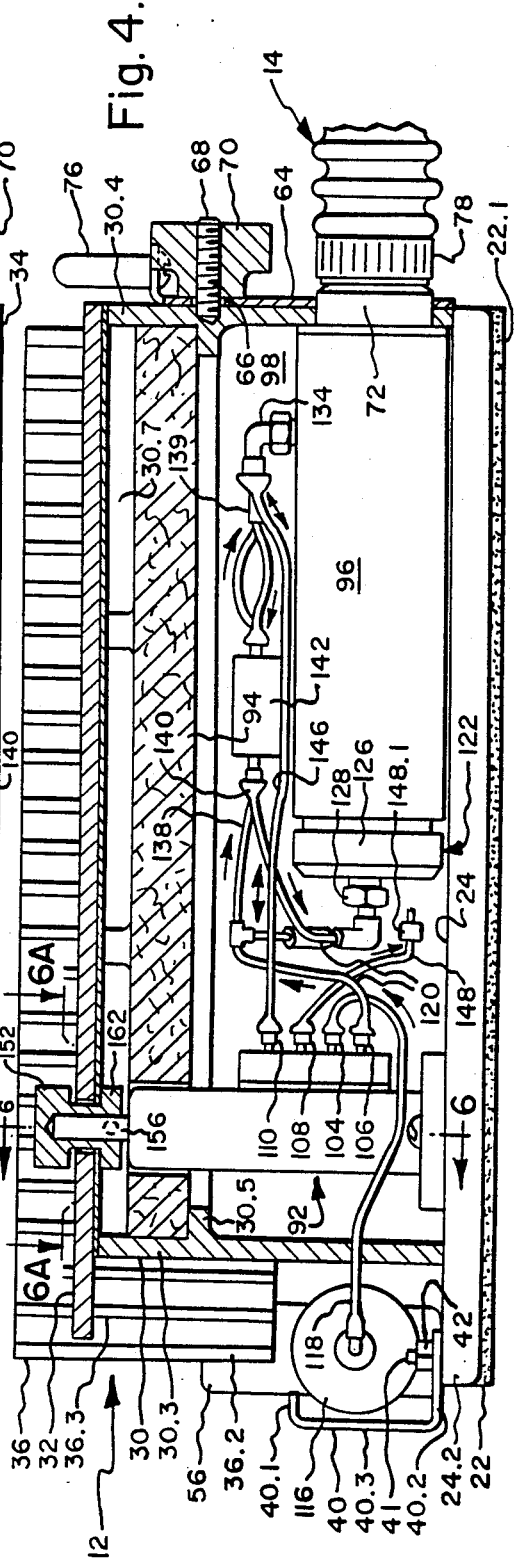

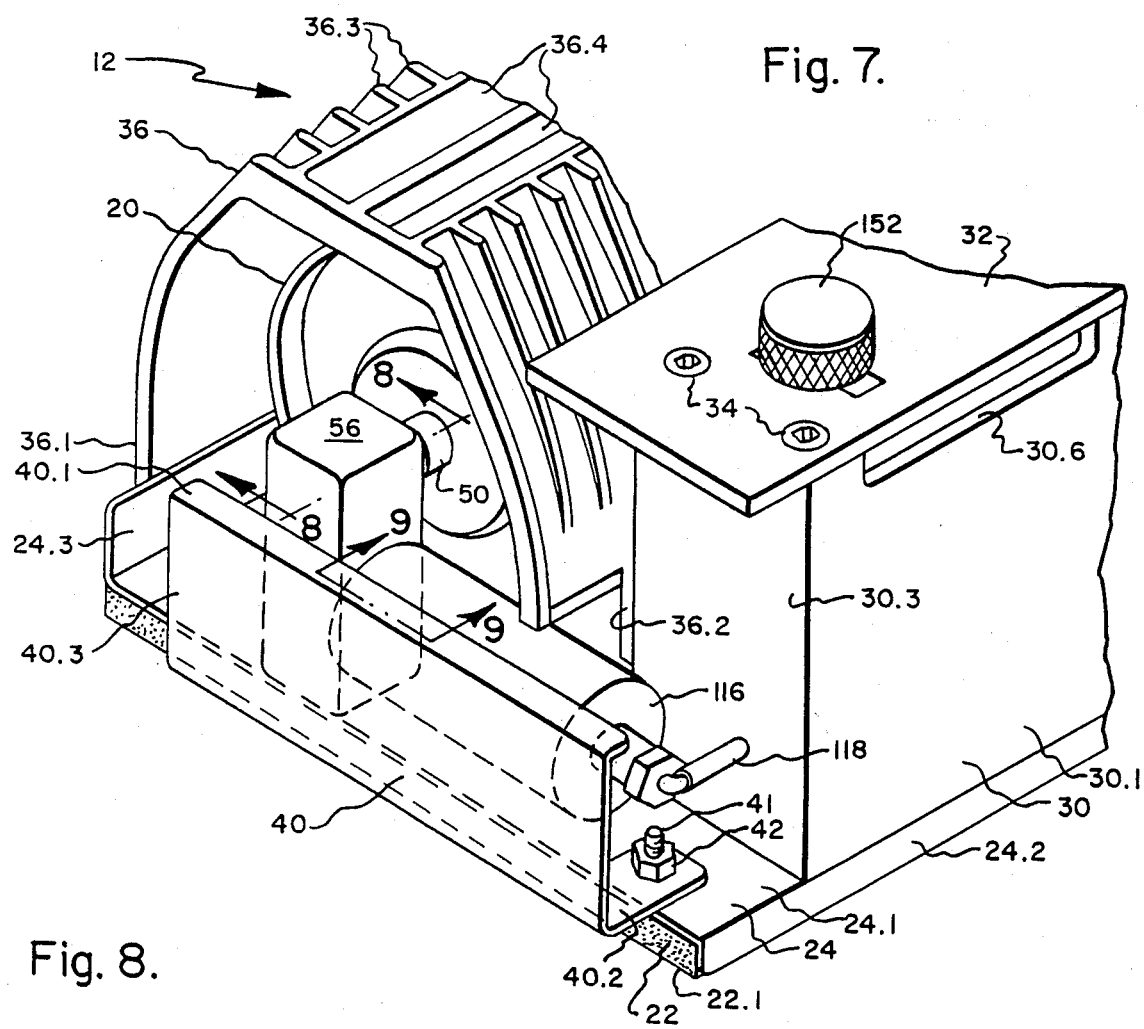
Fig. 7.
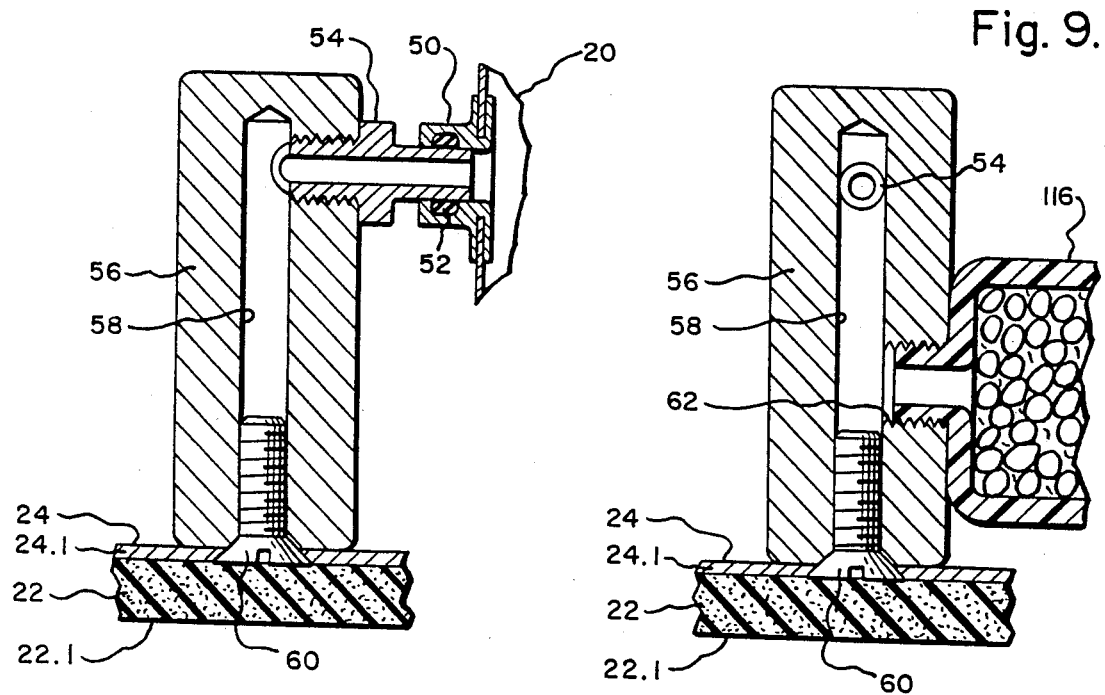
Fig. 8.
Fig. 9.

PORTABLE LIGHT WEIGHT COMPLETELY SELF-CONTAINED EMERGENCY SINGLE PATIENT VENTILATOR/RESUSCITATOR

FIELD OF THE INVENTION

The present invention relates generally to respiratory apparatus, and more particularly to a portable light weight completely self-contained emergency single patient ventilator/resuscitator which can be used at the scene of emergencies by persons with minimal training and yet will provide safe forced ventilation.

BACKGROUND OF THE INVENTION

While ventilators and/or resuscitators are well known in the art, these devices have been primarily developed for use in hospitals. Thus, such devices are typically fairly cumbersome, utilize the hospital oxygen supply system, and are typically plugged into an alternating current outlet in the hospital. These typical devices are neither self-contained nor portable. Additionally, they cannot be used in emergency situations by persons with minimal training.

In order to provide for treatment of patients experiencing respiratory distress at the scene, various techniques and equipment have been developed. One technique is mouth-to-mouth resuscitation. However, even with a one-way valve, the practitioner may find that this form of resuscitation is not only tiring but is also unpleasant. In addition, the oxygen content of the breaths to the patient is only about 16%. Furthermore, volume, pressure and breath rate delivered to the patient tend to be inconsistent.

Manual bagging is another manner of providing ventilation or resuscitation. However this form of respiratory therapy requires some training and is tiring after only a short time. Like mouth-to-mouth resuscitation, volume, pressure and breath rate delivered to the patient tend to be inconsistent. While cylinder oxygen may be utilized as a source of oxygen when using manual bagging, the oxygen cylinders are heavy and bulky, and they additionally require frequent maintenance to insure that a full charge is maintained.

If forced ventilation with a manual flow valve is used in connection with cylinder oxygen, over pressurization of the patient is a possibility. Thus, resuscitation using cylinder oxygen typically should only be attempted by persons with proper training.

In order to overcome the disadvantages of mouth-to-mouth resuscitation, manual bagging (either with or without cylinder oxygen) and other apparatus developed for use at the scene of an emergency, a portable apparatus has been developed, which apparatus is shown in U.S. Pat. No. 4,651,731, the subject matter of which is incorporated herein by reference thereto. This apparatus is a completely self-contained portable single patient ventilator/resuscitator which utilizes a solid state oxygen generator in the form of a chlorate candle. Several adjustable features and various modes of ventilation are provided on the above apparatus and thus the patented apparatus is required to be used by persons with respiratory training. The patented device, while considerably less costly than those units typically utilized in hospitals, it is also more expensive than needed to be used safely by people with only minimal respiratory training.

OBJECTS AND SUMMARY OF THE INVENTION

It is an object of the present invention to provide a portable light weight completely self-contained emergency single patient ventilator/resuscitator unit which can be safely used in emergencies for cases of respiratory distress or arrest and for injury trauma victims by persons with minimal training.

It is a further object of the present invention to provide an apparatus of the type referred to above which is less complex and lower in cost than prior known devices.

The above objects and other objects of this invention are achieved by providing a housing which supports a solid state oxygen generator in the form of a chlorate candle, the housing additionally supporting a pump in the form of a venturi ejector, a two-position valve, and suitable primary controls which are utilized to automatically control the inspiratory:expiratory ratio, the inspiratory time, the expiratory time, the breaths per minute, the flow rate, the tidal volume, the minute volume, etc. Various fluid lines interconnect the valve with the power supply, the pump, and controls. In accordance with one feature of this invention, the controls include a fixed volume timing chamber which is disposed about the venturi ejector. In accordance with another feature of this invention, the housing is provided with a void adjacent the timing chamber, which void acts as an accumulator during the expiratory cycle. In accordance with another feature of this invention, the two-position valve may be switched from its expiratory position to its inspiratory position against full pilot line pressure by a push button or the like should the operator desire to give extra breaths or sigh breaths. In addition, the push button can be so positioned that the valve may be maintained in its inspiratory position, which may be desirable when the patient is breathing on his own and only requires extra oxygen over that which he would normally receive from ambient air.

The foregoing features and other objects and advantages of the present invention will be more fully understood after a consideration of the following detailed description taken in conjunction with the accompanying drawings in which a preferred form of this invention is illustrated.

BRIEF DESCRIPTION OF THE DRAWINGS

FIG. 2 is an end view of the housing assembly shown in FIG. 1.

FIG. 3 is a top view of the housing assembly, this view being taken generally along the line 3—3 in FIG. 2.

FIG. 4 is a sectional view taken generally along 4—4 in FIG. 2.

FIG. 5 is a section view through the pump mounted within the housing assembly, this veiw being taken generally along the line 5—5 in FIG. 2.

FIG. 6A is a detail view taken generally along the line 6A—6A in FIG. 4.

FIG. 7 is a perspective view of the left hand end of the housing assembly shown in FIG. 1.

FIGS. 8 and 9 are sectional views taken generally along the lines 8—8 and 9—9 in FIG. 7, respectively.

DETAILED DESCRIPTION

Figure 1:
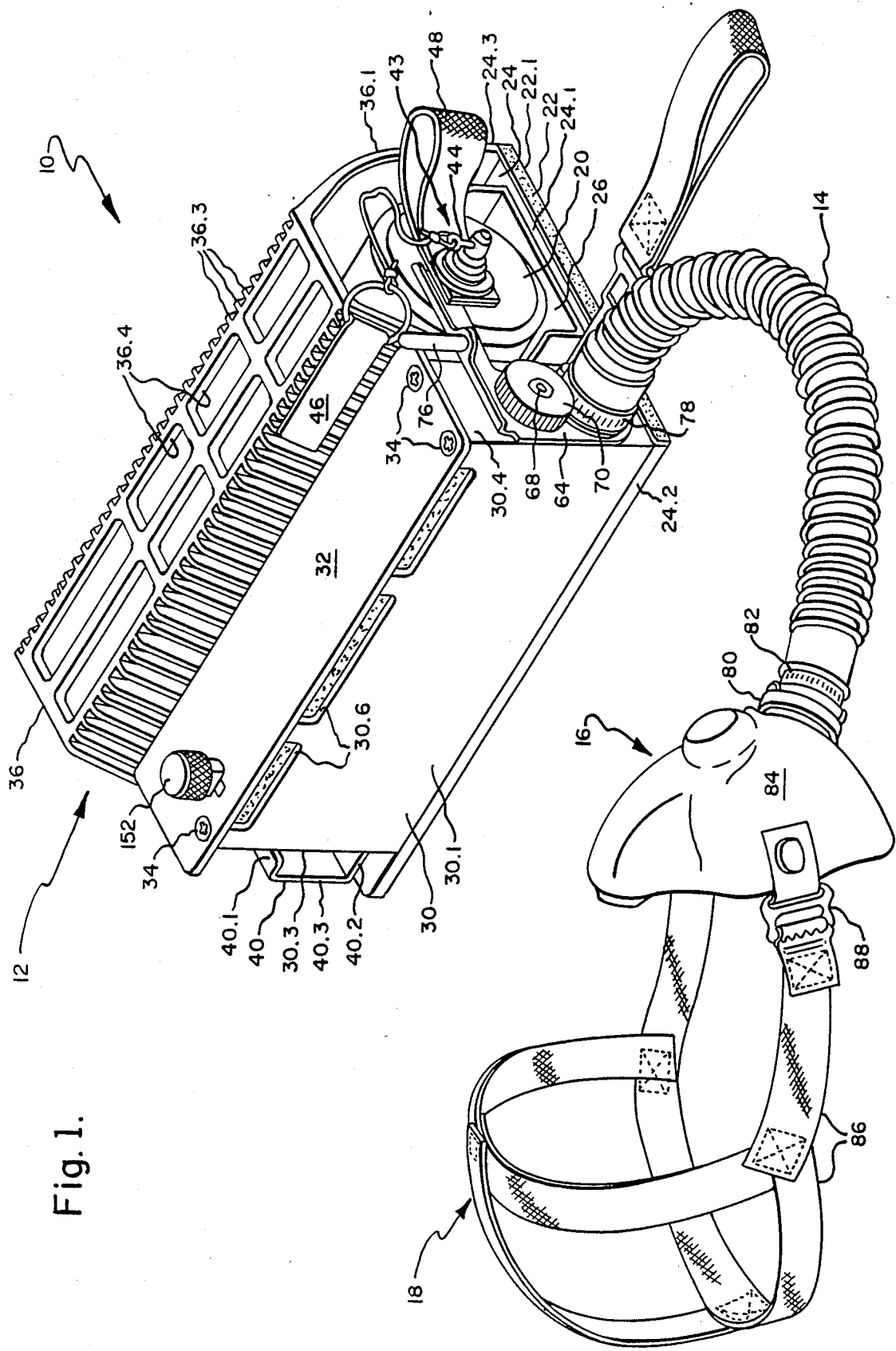
FIG. 1 is a perspective view of the apparatus of this invention, which apparatus includes a housing assembly, outlet tube, inhalation/exhalation valve, oral/nasal mask and head harness.

Referring first to FIG. 1, the portable light weight completely self-contained emergency single patient ventilator/resuscitator apparatus of this invention is indicated generally at 10. The apparatus includes as its major components a housing assembly indicated generally at 12, outlet tubing 14, an oral/nasal mask assembly indicated generally at 16 and a head harness assembly indicated generally at 18. Mounted within a portion of the housing assembly 12 is a solid state oxygen generator in the form of a chlorate candle 20, the candle acting as a power supply to the apparatus during its operation. A number of other major components of the ventilator/resuscitator of this invention are also mounted within the housing assembly as will be brought out below.

The housing assembly consists of a number of components, including a metal mounting plate or base plate 24 overlying a rubber-like foam pad 22, the base plate 24 being provided with an intermediate portion 24.1 which is adapted to be disposed parallel to the lower surface 22.1 of the pad 22, a forward downwardly extending flange 24.2 and a rear upwardly extending flange 24.3. Overlying the intermediate portion 24.1 of the base plate 24 is an elongated saddle bracket 26. The saddle bracket is secured to the base plate 24 by suitable fasteners 28 which pass through apertures in the saddle bracket and base plate.

Mounted on the intermediate portion 24.1 between the forward flange 24.2 and the forward side of saddle bracket 26 is a box-like member 30 which is rigidly secured at its lower end to the intermediate portion 24.1, the box-like member having front and rear sides 30.1 and 30.2, respectively, and also left and right sides 30.3, 30.4, respectively. Disposed between the upper and lower ends of each of the sides is an inwardly extending apertured flange 30.5. The front and rear walls are also provided with upper notches or cutouts 30.6, 30.7, respectively, which cutouts permit the entry of air into the box-like member. The rear side wall 30.2 is provided with rearwardly extending buttons or studs 30.8 (only one being shown). The top of the box-like member is closed by a cover 32 which is secured in place by fasteners 34.

A somewhat flexible molded plastic candle enclosing member 36 is secured at its rear side 36.1 (to the right in FIG. 2) to the upwardly extending flange 24.3 by fasteners 38 (only one being shown). A forward portion 36.2 of the enclosing member is provided with suitable apertures which receive the buttons 30.8. As can be seen best from FIG. 1 the upper intermediate portion of the candle enclosing member 36 is provided with suitable ribs 36.3 and apertures 36.4 to permit the dissipation of the heat which evolves when the candle 20 is in operation. Finally, the housing additionally includes a shield or bracket 40 which is mounted upon the left-hand end of the metal plate 24 to the left of the box-like member 30 as best seen in FIGS. 3, 4 and 7. The shield has upper and lower parallel portions 40.1 and 40.2 joined by an intermediate portion 40.3. The shield is secured by screws 41 (only one of which is shown) that pass through weld nuts 42 secured to an upper surface of the portion 40.2, the head of the screw bearing against a lower surface of the intermediate portion 24.1 of the plate 24.

The chlorate candle, as is conventional, is provided with a firing mechanism at one end, the firing mechanism being indicated generally at 43 in FIG. 1, the mechanism including a pin 44 which is connected to a lanyard assembly 46. By pulling the lanyard assembly 46 and the associated pin 44 the operation of the chlorate candle can be initiated. The chlorate candle 20 is also provided with a fabric handle 48 to facilitate its removal from the housing. The end of the chlorate candle remote from the firing mechanism 43 is provided with an outlet port 50 (FIGS. 7 and 8) which includes an O-ring 52 or the like. A fitting 54, which can be telescopically received by the outlet port 50 as best shown in FIG. 8, is carried by a machined element 56, which element is provided with a bore 58, the fitting 54 being tapped through the element into the bore 58. The machined element 56 is secured to the intermediate portion 24.1 by a screw fastener 60 which along with a sealant (not shown), closes off the bore 58. Finally, the machined element 56 is also provided with a tapped aperture 62 (FIG. 9) disposed at right angles to the fitting 54, the aperture 62 also being disposed below the fitting 54.

When the candle is assembled into the housing it is placed upon the saddle 26 and is slid from the right to the left until the outlet port 50 is telescoped over fitting 54. The candle is now secured in place by swinging an L-shaped retainer 64 (FIG. 2) from an inoperative position shown in dot-dash lines to its operative position shown in full lines. To this end the retainer 64 is provided with a curved slot 66 which receives a screw 68 (FIG. 4), which screw carries an enlarged knurled head 70. One end of the L-shaped retainer 64 is provided with a circular aperture which is disposed about a cylindrical tubular element 72 which projects outwardly of the right side wall 30.4 of the box-like member. The L-shaped retainer is additionally provided with an inwardly extending tab 74 (FIG. 3) which is adapted to bear against the right-hand end of the chlorate candle 20. Finally, the L-shaped retainer 64 is also provided with a handle 76 to facilitate its movement between its operative or full line position shown in FIG. 2 to or from its inoperative position shown in dot-dash lines in FIG. 2.

The outlet tubing 14 is of conventional construction and is secured about a reduced diameter portion 72.1 of the cylindrical tubular element 72 by a conventional clamp 78 which is of the type typically used in an automobile to secure radiator hoses and the like. The other end of the outlet tubing is secured to a reduced diameter portion of a combination inhalation exhalation valve 80 by a clamp 82 which is similar to the clamp 78. The valve 80 forms a portion of the oral/nasal mask assembly, the valve in turn being secured to a face piece 84 in any conventional manner not relevant to the present invention. The face piece 84 can in turn be secured about the face of a patient by the head harness which includes straps 86 and buckles 88 (only one of which is shown).

Mounted within the box-like member 30 are a number of components essential for the delivery of oxygen from the chlorate candle to the patient. These components include pump means indicated generally at 90 (FIG. 5), a two-position valve indicated generally at 92 (FIG. 4), primary control means indicated generally at 93, and interconnecting fluid lines. In addition, a filter 94 is supported upon the flange 30.5, the filter being of such a height that its top edge, when supported on the flange, is disposed immediately below the notches or cutouts 30.6 and 30.7 in the boxlike member 30. The pump means 90 is mounted within a generally rectangular enclosure 96 which has a length generally the length of the pump means and a width substantially equal to the width of the box-like member 30 between the front and rear walls 30.1 and 30.2, respectively. It can be seen from an inspection of the drawings that there is thus an internal void 98 within the housing assembly 12, the void being that volume of empty space within the box-like member 30 below the filter 94, which void is only partially filled by the rectangular enclosure 96, two-position valve means 92 and various fluid lines and control elements. This void defines an accumulator, and also may also act as a fluid line.

The two-position valve 92 is a typical air piloted relay spool valve. The valve includes a valve spool 100 (FIG. 6) mounted within a suitable valve body 102. When the valve spool is in its expiratory position, shown in FIG. 6, land 100.1 of valve spool 100 will lie between an inlet port 104 and a first outlet port 106 in the valve body 102. In addition, land 100.2 of the valve spool 100 will lie between a second outlet port 108 and a pilot line port 110 as it also does in the inspiratory position. The expiratory position is attained by introducing a fluid under pressure from a source of pilot line pressure through port 110 sufficient to bias the valve spool upwardly to the position illustrated against the downward force exerted by relay spring 112 and also the downward force exerted by detent ball 113 on a groove 114 of the valve spool. This position will be maintained until the downward force exerted by the relay spring 112 exceeds the upward force exerted by spring biased ball 113 on a groove 114 plus the upward force exerted on valve spool 100 by the pilot line pressure, at which time the valve spool will shift away from the position shown in FIG. 6 to the position shown schematically in FIG. 10. When the valve spool is in the FIG. 6 or expiratory position the inlet port 104 is effectively in fluid communication with the second outlet port 108. When the valve is in the inspiratory position shown in FIG. 10 the inlet port 104 is in fluid communication with the first outlet port 106. The operation of the two-position valve will be more fully described below.

Figure 10:
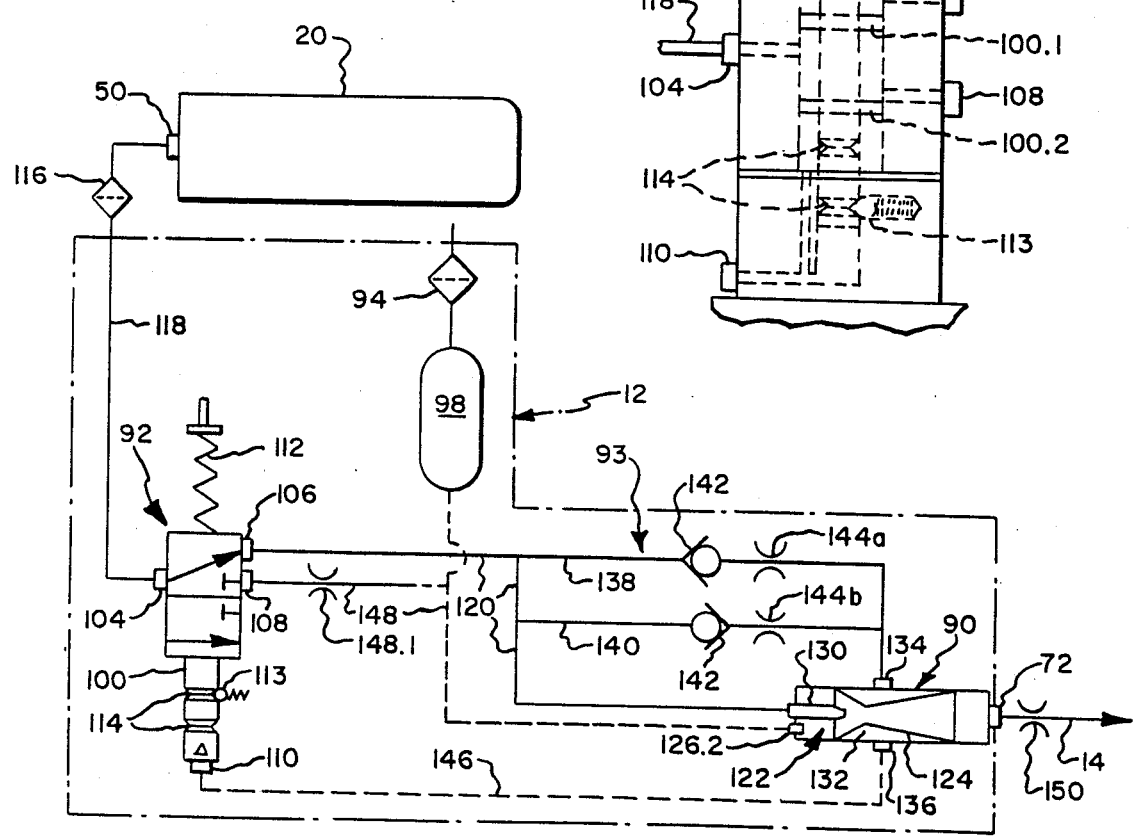
FIG. 10 is a somewhat schematic fluid circuit system diagram illustrating the present invention when it is in its inspiratory position.

In operation, the operator will place the mask and head harness on a patient and initiate operation of the ventilator/resuscitator by pulling on the lanyard assembly 46 to remove the pin 44 to cause the operation of the firing mechanism 43, which will in turn cause the chlorate candle 20 to commence its operation. Once the chlorate candle commences operation it will discharge oxygen through outlet port 50, bore 58 in machine element 56, and then through the tapped aperture 62 into a dryer 116. From the dryer the oxygen will then pass through a first or power supply line 118 to the inlet port 104 of the two-position valve 92. As can best be seen from FIGS. 3 and 4 the power supply line 118 passes through the left hand sidewall 30.3 of the box-like member 30. The oxygen, which is discharged at approximately 50 psi, provides sufficient power for the functioning of the present apparatus. When the two-position valve 92 is in its inspiratory position as shown in FIG. 10, oxygen delivered to the inlet port 104 will be delivered to the first outlet port 106. From the first outlet port 106 oxyen will be delivered through inspiratory fluid line 120 to the driving portion of the pump means 90. the driving portion being indicated generally at 122. In this connection it should be noted that the pump means is of the type which is sometimes called a venturi pump, and sometimes called an ejector. In any event, the pump is provided with a venturi portion 124 (FIG. 5) which extends from a narrow portion 124.1 adjacent its left hand end to an enlarged portion 124.2 at is right hand end. Immediately to the left of the narrow portion 124.1 is a bell-shaped portion 124.3. The bell-shaped portion and the enlarged portion are both adhesively secured to the rectangular enclosure 96. Disposed to the left of the bell-shaped portion 124.3 (as shown in FIG. 5) is an end cap 126 which is provided with a central aperture 126.1 and a plurality of apertures 126.2 disposed between the central aperture 126.1 and the periphery 126.3 of the end cap. Gas from the accumulator 98 may pass through the apertures 126.2 into the venturi. The inspiratory fluid line 120 is connected with a port defining element 128 threaded into the left hand end of the central aperture 126.1. A jet orifice 130 is threaded into the right hand end of the central aperture 126.1, the jet orifice acting as the driving portion of the venturi or ejector pump. When oxygen flows through the jet and into the narrow portion 124.1 of the venturi gases from the accumulator 98 will be drawn into the bell-shaped portion 124.3 and will be caused to be mixed with the oxygen within the venturi as it is moved through the pump. The bell-shaped portion 124.3 can be considered to be the suction portion of the pump, and the enlarged portion 124.2 can be considered to be the discharge portion.

It can be seen that there is a chamber 132 between the rectangular enclosure 96 and the venturi portion 124 of the pump, this chamber serving as a fixed volume timing chamber. First and second ports 134, 136, extend through the rectangular enclosure 96 to the chamber 132. First and second control lines extend from the inspiratory fluid line 120 to a Y-fitting 139 and then to the first port 134, each of the first and second control lines 138, 140, being provided with a check valve 142 and a fixed orifice restrictor, either 144a or 144b, respectively. The restrictors regulate the flow into and out of timing chamber 132 and can be selected to provide any reasonable inspiratory and expiratory time. For example, a normal inspiratory time of about 1.33 seconds and an expiratory rate of 2.66 seconds. As can be seen from FIG. 10 the check valve 142 in the first control line 138 will permit flow only from the inspiratory fluid line 120 through restrictor 144a to the first port 134. Similarly, the check valve 142 in the second control line 140 will permit fluid flow only from the first port 134 through restrictor 144b to the inspiratory fluid line 120. A pilot line 146 extends from the second port 136 to pilot line port 110 on the two-position valve 92.

Figure 6:
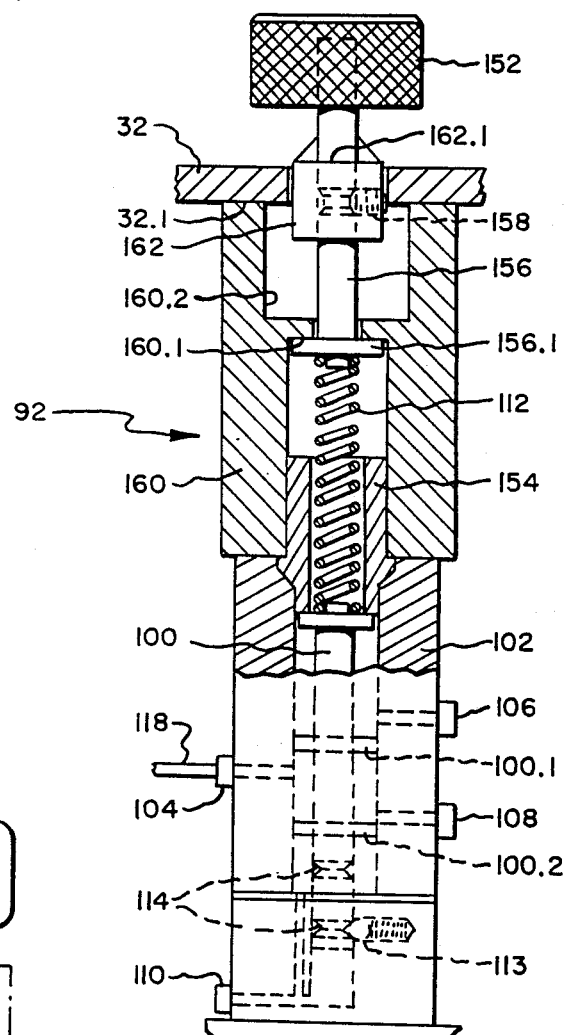
FIG. 6 is a view of a portion of the apparatus mounted within the housing assembly, this view being taken generally along the line 6—6 in FIG. 4, some parts being eliminated, and other parts being shown in section or somewhat schematically for purposes of clarity.

As oxygen is being delivered to the driving portion 122 of the pump means 90 a small portion of the oxygen is also flowing through the control line 138, past the first check valve 142, and first restrictor 144a through port 134 into the chamber 132. As the pressure builds up within the chamber 132 the pilot line pressure, which acts upon land 100.2, will eventually exceed the downward pressure exerted on the spool by the spring 112 which engages the upper end 100.3 of the spool and the detent ball 113 which engages one of two detent grooves 114. The greater pressure in the pilot line will cause the valve spool 100 to shift from its inspiratory position to its expiratory position, which position is shown in FIG. 6. When this position is achieved the other groove 114 will be engaged by the spring detent ball 113. Flow from the power supply 20 in line 118 will now be delivered through the second outlet port 108 into the supplemental air line 148. The supplemental air line 148 terminates within accumulator 98, the air line being provided with orifice 148.1 in order to maintain proper back pressure. It can be seen that when the valve is in the expiratory position that oxygen will be delivered to the void or accumulator 98 forcing air out of this area through the filter 94. After the valve 92 has shifted to its expiratory position the over pressure in the timing chamber 132 will be bled through port 134, restrictor 144b and also through the check valve 142 in control line 140, and then through the inspiratory line 120 to the jet orifice 122. When the pressure in the timing volume chamber 132 has fallen below a predetermined amount the spring 112 will then cause the valve spool to be shifted back to its inspiratory position. When the valve 92 is in the inspiratory position the oxygen delivered to the accumulator will now be drawn into the venturi through the peripheral ports 126.2. It should be noted at this point that in FIG. 10 that a portion of the supplemental air line means 148 is shown in phantom. As can be seen from the actual construction illustrated in FIGS. 3 and 4 there is only a short line 148 provided with restrictor 148.1, and in reality the phantom lines illustrated in the schematic drawing correspond to the void 98. The flow rate to the patient is additionally regulated by providing a restrictor element 150 (FIG. 5) in the cylindrical tubular element 72, which tubular element is an extension of the rectangular enclosure 96. This restrictor element regulates the volume of air delivered to the patient and may be set so that only, for example, 5 liters per minute of oxygen and air are delivered to the patient. It should be noted at this point that the primary control means 93 include the restrictors 144, check valves 142, fixed volume chamber 132, line 148, restrictor element 150 as well as various other properly sized elements. Control elements 144 and 150 may be varied at the factory or by a service technician to vary inspiratory and expiratory times, tidal volumes, flow rates, etc.

It should be appreciated that without intervention, and during the operation of the power supply 20, that the apparatus of this invention will continue to cycle as long as oxygen under pressure is being discharged from the chlorate candle. By properly selecting the restrictors 144a, 144b, and 150 in conjunction with the size of the fixed volume chamber 132 it is possible to set up the device in various manners. For example, the inspiratory time may initially be set to 1.33 seconds and the expiratory time to 2.66 seconds, providing an I:E ratio of approximately 1:2 and which would in turn deliver approximately 15 breaths per minute. After the ventilator/resuscitator of this invention has been in use for a period of time it has been found by testing that the oxygen delivered to the patient may be as high as 92%.

It may be desirable, during the expiratory time, or at the end of the inspiratory time to give additional breathing time, to provide either extra breaths or to give sigh breaths. This feature is incorporated into the apparatus of this invention and is accomplished by pressing down on knob 152 which forms part of a secondary control means. When knob 152 is depressed it will cause the spring 112 to become additionally compressed, thereby increasing the spring pressure exerted upon the spool 100 to such an extent that the spool will be shifted from its expiratory position shown in FIG. 6 to its inspiratory position shown in FIG. 10, the spring pressure being such that it exceeds the force exerted by the pilot line pressure on the valve 92. The structural relationship between the knob 152 and the two-position valve 92 is best shown in FIG. 6. In this Figure it can be seen that the lower portion of the spring 112 extends through a spring retainer 154, the upper end of the spring bearing against a flange portion 156.1 of knob stem 156, the knob 152 being suitably mounted on the stem by means of a set screw 158. Upward movement of the flange portion 156.1 is limited by an internal flange 160.1 of a valve body extension 160, which extension is provided with a cylindrical opening 160.2 which receives a lower portion 162 of knob 152.

At times when the patient is breathing and forced ventilation is not required, such as in the cases of injury trauma, it may be desirable to provide a constant flow of mixedair and oxygen to the patient. This is accomplished by maintaining the knob 152 in its full down position. At this time the mask must be loose on the face so that the patient can breath in the O₂/air provided, but can exhale easily against the constant flow. To maintain the knob 152 down, the lower portion 162, which is elongated in one direction, is shifted below an elongated aperture 164 in cover 32 (FIG. 6A). Thus, when the knob 152 is pushed down, the upper edge 162.1 of the lower portion 162 will be disposed below the lower surface 32.1 of the cover 32. It is now only necessary to rotate the knob 152 a few degrees to trap the lower portion 162 below the cover 32 thus maintaining the two-position valve means in its inspiratory position shown in FIG. 10.

While a preferred embodiment in which the principles of the present invention have been incorporated is shown and described above, it is to be understood that widely differing means may be employed in the practice of the broader aspects of this invention. Thus, it is to be understood that this invention is not to be limited to the particular details shown and described above, but that, in fact, widely differing means may be employed in the broader aspects of this invention.

What is claimed is:

1. A portable, light weight, completely self-contained emergency single patient ventilator/resuscitator apparatus capable of operating without attention in a resuscitating mode during operation of a power supply to cyclically force air and oxygen into a patient's respiratory cavity during an inspiratory mode and then to permit the patient's respiratory cavity to expire during an expiratory mode; the apparatus comprising:

a housing assembly, a portion of the housing assembly defining an accumulator open at first and second ends;

a power supply carried by the housing assembly and having a discharge portion, the power supply being capable when in operation of discharging oxygen through the discharge portion over a period of time at a pressure sufficiently great to force oxygen into a patient's lungs;

pump means carried by the housing assembly, the pump means having a suction portion, a discharge portion and a driving portion, the pump means being capable of being operated when the driving portion is operatively interconnected to the discharge portion of the power supply when the power supply is in operation, the pump means when being operated causing ambient air to be drawn into the pump means through the accumulator and suction portion, the ambient air to be mixed with oxygen within the pump means, and the mixed air and oxygen to be discharged through the discharge portion;

a two-position valve shiftable between inspiratory and expiratory positions and including an inlet port and first and second outlet ports, the valve when in the inspiratory position connecting the inlet port with the first outlet port, and the valve when in the expiratory position connecting the inlet port with the second outlet port;

first line means extending from the discharge portion of the power supply to the inlet port of the two-position valve;

further line means extending from the first and second outlet ports of the two-position valve to the driving portion of the pump means, the first end of the accumulator and to the suction portion of the pump;

outlet tubing having one end portion connected to the discharge portion of the pump means, and another end portion being adapted to be interconnected to a patient whereby mixed air and oxygen may be delivered to the patient during inspiratory operation of the ventilator/resuscitator; and control means interconnected with the two-position valve and capable of shifting the two-position valve between inspiratory and expiratory positions.

2. The apparatus as set forth in claim 1 wherein the housing assembly is further provided with a filter disposed between the second end of the accumulator and ambient air, the pump means when powered causing ambient air to be drawn into the pump means through the filter, accumulator, and suction portion, respectively.

3. The apparatus as set forth in claim 1 wherein the control means includes a primary control means interconnected with the further line means and the two-position valve, the primary control means being capable of shifting the two-position valve from one position to another position after a predetermined time period.

4. The apparatus as set forth in claim 3 wherein the primary control means includes a fixed volume timing chamber disposed about the pump means.

5. The apparatus as set forth in claim 4 wherein the further line means includes inspiratory line means which extends from the first outlet port to the driving portion of the pump means and supplemental air line means which extends from the second outlet port to the first end of the accumulator and to the suction side of the pump.

6. The apparatus as set forth in claim 5 wherein the timing chamber is provided with first and second ports, and wherein the primary control means further includes first and second control lines extending between the inspiratory line means and the first port on the timing chamber, each of the first and second control lines including a check valve and a fixed orifice restrictor.

7. The apparatus as set forth in claim 6 wherein the control means further includes a pilot line extending between the second port on the timing chamber and one end of the two-position valve.

8. The apparatus as set forth in claim 7 further characterized by the provision of manually operable secondary control means capable when suitably operated of shifting the two-position valve from its expiratory position to its inspiratory position against full pilot line pressure.

9. A portable light weight, completely self-contained emergency single patient ventilaftor/resuscitator apparatus capable of operating without attention in a resuscitating mode during operation of a power supply to cyclically force air and oxygen into a patient's respiratory cavity during an inspiratory mode and then to permit the patient's respiratory cavity to expire during an expiratory mode; the ventilator/resuscitator comprising:

a housing assembly;

power supply carried by the housing assembly and capable when in operation of discharging oxygen through a discharge portion over a period of time at a pressure sufficiently great to force oxygen into a patient's lungs;

pump means disposed within the housing assembly, the pump means having a suction portion, a discharge portion and a driving portion, the pump means being capable of being operated when the driving portion is operatively interconnected to the discharge portion of the power supply and the power supply is in operation, the pump means when being operated causing ambient air to be drawn into the pump means through the suction portion, the ambient air to be mixed with oxygen within the pump means, and the mixed air and oxygen to be discharged through the discharge portion;

two-position valve shiftable between inspiratory and expiratory positions and including an inlet port and first and second outlet ports, the valve when in the inspiratory position connecting the inlet port with the first outlet port, and the valve when in the expiratory position connecting the inlet port with the second outlet port;

first line means extending from the discharge portion of the power supply to the inlet port of the two-position valve;

further line means extending from the first and second outlet ports of the two-position valve to the driving portion of the pump means, to a source of ambient air, and to the suction side of the pump;

control means interconnected with the further line means and the two-position valve, the control means being capable of shifting the two-position valve from one position to another position after a predetermined time period, the control means including primary control means housing a fixed volume timing chamber disposed about the pump means; and outlet tubing having one end portion connected to the discharge portion of the pump means, and another end portion being adapted to be interconnected to a patient whereby mixed air and oxygen may be delivered to the patient during inspiratory operation of the ventilator/resuscitator.

10. The apparatus as set forth in claim 9 wherein the fixed timing volume chamber has first and second ports, the control further including first and second control lines extending between the further line means and the first port on the timing chamber, each of the first and second control lines including a check valve and a restrictor, and a pilot line extending between the second port on the timing chamber and one end of the two-position valve.

11. The apparatus as set forth in claim 10 further characterized by the provision of manually operable secondary control means capable when suitably operated of shifting the two-position valve from its expiratory position against full pilot line pressure.

12. The apparatus as set forth in claim 9 wherein the housing assembly is provided with an internal void, the second outlet port of the two-position valve being in communication with the void via the further line means when the two-position valve is i its expiratory position whereby oxygen discharged by the power supply will be received within the void, the void acting as an accumulator, the void being in communication with the source of ambient air.

13. The apparatus as set forth in claim 12 wherein the housing assembly carries a filter disposed between the void and the source ambient air.

14. The apparatus set forth in claim 12 wherein the further line means is provide with a restrictor capable of maintaining proper back pressure.

15. The apparatus as set forth in claim 9 wherein the further line means includes inspiratory line means which extends from the first outlet port of the two-position valve to the driving portion of the pump means, and supplemental air line means in the form of a void within the housing assembly, the supplemental air line means extending to the suction side of the pump.

16. A portable, light-weight, completely self-contained emergency single patient ventilator/resuscitator apparatus capable of operating without attention in a resuscitating mode during operation of a power supply to cyclically force air and oxygen into a patient's respiratory cavity during an inspiratory mode and then to permit the patient's respiratory cavity to expire during an expiratory mode; the ventilator/resuscitator comprising:
    a housing assembly;
    power supply carried by the housing assembly and capable when in operation of discharging oxygen through a discharge portion over a period of time at a pressure sufficiently great to force oxygen into a patient's lungs;
    pump means disposed within the housing assembly, the pump means having a suction portion, a discharge portion and a driving portion, the pump means being capable of being operated when the driving portion is operatively interconnected to the discharge portion of the power supply and the power supply is in operation, the pump means when being operated causing ambient air to be drawn into the pump means through the suction portion, the ambient air to be mixed with oxygen within the pump means, and the mixed air and oxygen to be discharged through the discharge portion;
    a two-position valve shiftable between inspiratory and expiratory positions and including an inlet port an first and second outlet ports, the valve when in the inspiratory position connecting the inlet port with the first outlet port, and the valve when in the expiratory position connecting the inlet port with the second outlet port;
    power supply line means extending from the discharge portion of the power supply to the inlet port of the two-position valve;
    inspiratory line means extending from the first outlet port of the two-position valve to the driving portion of the pump means and capable of delivering oxygen to the driving portion of the pump when the two-position valve is in its inspiratory position;
    supplemental air line means interconnecting a source of ambient air with the suction side of the pump;
    control means interconnected with the inspiratory line means and the two-position valve, the control means including primary control means capable of shifting the two-position valve from one position to another position after a predetermined time period, the primary control means including a timing volume chamber having first and second timing chamber ports, first and second control lines extending between the inspiratory line means and one of the timing chamber ports, each of the first and second control lines including a check valve and a fixed orifice restrictor, and pilot line means extending between the other timing chamber port and the two-position valve; and
    outlet tubing having one end portion connected to the discharge portion of the pump means, and another end portion being adapted to be interconnected to a patient whereby air and oxygen may be delivered to the patient during inspiratory operation of the ventilator/resuscitator.

17. The apparatus as set forth in claim 16 wherein the supplemental air line means includes a void within the housing assembly which may act as an accumulator.

18. The apparatus as set forth in claim 17 wherein the supplemental air line means further includes a supplementary fluid line connected to the second outlet port of the two-position valve whereby oxygen may be discharged into the void when the two-position valve is in its expiratory position.

19. The apparatus as set forth in claim 18 wherein the supplementary fluid line is provided with a restrictor capable of maintaining proper back pressure.

20. The apparatus as set forth in claim 17 wherein the void is interconnected with ambient air disposed to the exterior of the housing assembly, the housing assembly carrying a filter which is disposed between the accumulator void and ambient air.

21. The apparatus as set forth in claim 16 further characterized by the provision of manually operable secondary control means capable when suitably operated of either shifting the two-position valve from its expiratory position to its inspiratory position against full pilot line pressure, or of maintaining the two-position valve in its inspiratory position against full pilot line pressure, the secondary control means being carried by the housing assembly.

22. A portable, light weight, completely self-contained emergency single patient ventilator/resuscitator apparatus capable of operating either with or without attention; the ventilator/resuscitator comprising:
    a housing assembly;
    power supply carried by the housing assembly and capable when in operation of discharging oxygen through a discharge portion over a period of time at a pressure sufficiently great to force oxygen into a patient's lungs;
    pump means disposed within the housing assembly, the pump means having a suction portion, a discharge portion and a driving portion, the pump means being capable of being operated when the driving portion is operatively interconnected to the discharge portion of the power supply and the power supply is in operation, the pump means when being operated causing ambient air to be drawn into the pump means through the suction portion, the ambient air to be mixed with oxygen within the pump means, and the mixed air and oxygen to be discharged through the discharge portion;

a two-position valve shiftable between inspiratory and expiratory positions and including an inlet port and first and second outlet ports, the valve when in the inspiratory position connecting the inlet port with the first outlet port, and the valve when in the expiratory position connecting the inlet port with the second outlet port, the two-position valve normally being spring biased to its inspiratory position;

power supply line means extending from the discharge portion of the power supply to the inlet port of the two-position valve;

inspiratory line means extending from the first outlet port of the two-position valve to the driving portion of the pump means;

supplemental air line means interconnected at one end to a source of ambient air and extending to the suction side of the pump;

primary control means including a pilot line interconnected with the two-position valve and when suitably pressurized being capable of shifting the two-position valve against spring bias from its inspiratory position to its expiratory position, and when not suitably pressurized permitting spring bias to dispose the valve in its inspiratory position;

manually operable secondary control means capable when suitably operated of shifting the two-position valve from its expiratory position to its inspiratory position against full pilot line pressure; and outlet tubing having one end portion connected to the discharge portion of the pump means, and another end portion being adapted to be interconnected to a patient whereby air and oxygen may be delivered to the patient during inspiratory operation of the ventilator/resuscitator.

23. The apparatus as set forth in claim 22 wherein the manually operable secondary control means is a push button which bears against that spring which biases the two-position valve to its inspiratory position, the push button capable of being locked in its down position.

* * * * *

UNITED STATES PATENT AND TRADEMARK OFFICE
CERTIFICATE OF CORRECTION

PATENT NO. : 4,905,688

DATED : March 6, 1990

INVENTOR(S) : Reno L. Vicenzi et al

It is certified that error appears in the above-identified patent and that said Letters Patent is hereby corrected as shown below:

IN THE CLAIMS:

Column 10, line 8, Claim 9, line 2, "ventilaftor" should be --ventilator--.

Column 11, line 8, Claim 11, line 5, after position insert --to its inspiratory position--.

Column 11, line 22, Claim 14, line 2, "provide should be --provided--.

Signed and Sealed this

Seventh Day of May, 1991

Attest:

HARRY F. MANBECK, JR.

*Attesting Officer*    Commissioner of Patents and Trademarks